United States Patent [19]

Poll

[11] Patent Number: 4,837,776
[45] Date of Patent: Jun. 6, 1989

[54] PROCESS FOR MEASURING THE VARIATIONS IN VOLUME OF FLUIDS, ESPECIALLY SHRINKAGE MEASUREMENTS IN SYNTHETIC RESINS DURING HARDENING AND A DEVICE FOR CARRYING OUT THE PROCESS

[75] Inventor: Dietmar Poll, Ste. Silvester, Switzerland

[73] Assignee: Ciba-Geigy Corporation, Ardsley, N.Y.

[21] Appl. No.: 129,517

[22] Filed: Dec. 7, 1987

[30] Foreign Application Priority Data

Dec. 16, 1986 [CH] Switzerland .................... 4994/86

[51] Int. Cl.$^4$ .................... G01N 3/18; G01N 25/02
[52] U.S. Cl. .................... 374/56; 374/51; 374/53; 73/866; 73/813
[58] Field of Search .................... 374/46, 47, 51, 53, 374/54, 55, 56; 73/813, 866, 823

[56] References Cited

U.S. PATENT DOCUMENTS

| | | | |
|---|---|---|---|
| 2,448,964 | 9/1948 | Dietert | 374/55 |
| 2,699,060 | 1/1955 | Safford | 374/51 |
| 2,904,994 | 9/1959 | Claxton | 374/53 |
| 3,248,925 | 5/1966 | Warfield | 374/56 |
| 3,589,167 | 6/1971 | Hill | 374/56 |
| 4,069,703 | 1/1978 | Standish et al. | 374/56 |
| 4,074,569 | 2/1978 | Sambrook et al. | 73/813 |
| 4,354,764 | 10/1982 | Achermann et al. | 374/46 |
| 4,700,561 | 10/1987 | Dougherty | 73/19 |

FOREIGN PATENT DOCUMENTS

| | | | |
|---|---|---|---|
| 523064 | 4/1931 | Fed. Rep. of Germany | 374/51 |
| 1316591 | 12/1961 | France . | |
| 2377042 | 8/1978 | France . | |
| 349926 | 9/1972 | U.S.S.R. | 374/51 |
| 379849 | 4/1973 | U.S.S.R. | 374/51 |
| 1275262 | 5/1972 | United Kingdom . | |

OTHER PUBLICATIONS

Zoller, et al., "Apparatus For Measuring Pressure-Volume-Temp. Relationships of Polymers to 350° C. And 2200 kg/cm$^2$" *Rev. Sci. Instr.* vol. 47, No. 8, pp. 948–952, 8–76.

Sereinig et al., "Method to Determine The Thermal Expansion of Epoxies, Inorganic Cements and Polyester Resins at Cryogenic Temp." *Cyrogenics* vol. 22 No. 1 pp. 17–201, –82.

*Primary Examiner*—William A. Cuchlinski, Jr.
*Assistant Examiner*—Thomas B. Will
*Attorney, Agent, or Firm*—Harry Falber

[57] ABSTRACT

In a process for measuring the variations in volume, especially shrinkage measurements in duroplastics during the hardening, the material to be measured is acted upon by such a pressure that a fully homogeneous test piece is obtained without any fractures or blisters. Simultaneously and independently from one another, the impinging pressure, the pressure exerted through the test piece on the floor, the temperature in the test piece and in its environs and the volume of the test piece are measured under non-isothermal conditions and fed into a digital unit. The device for carrying out this process has a measuring cylinder (5) with a measuring bore (12) and a measuring piston (10) which fits into this measuring bore and is acted upon by pressure, as well as a displacement detector (9) attached to the measuring piston, a temperature probe (14) in the measuring cylinder, a temperature probe (16) in the measuring bore for measuring the temperature in the test piece, a pressure gauge in the compressed air line, a pressure receiver (18) located at the end of the measuring bore which is opposite to the measuring piston and a heating means (13) for the measuring cylinder.

13 Claims, 1 Drawing Sheet

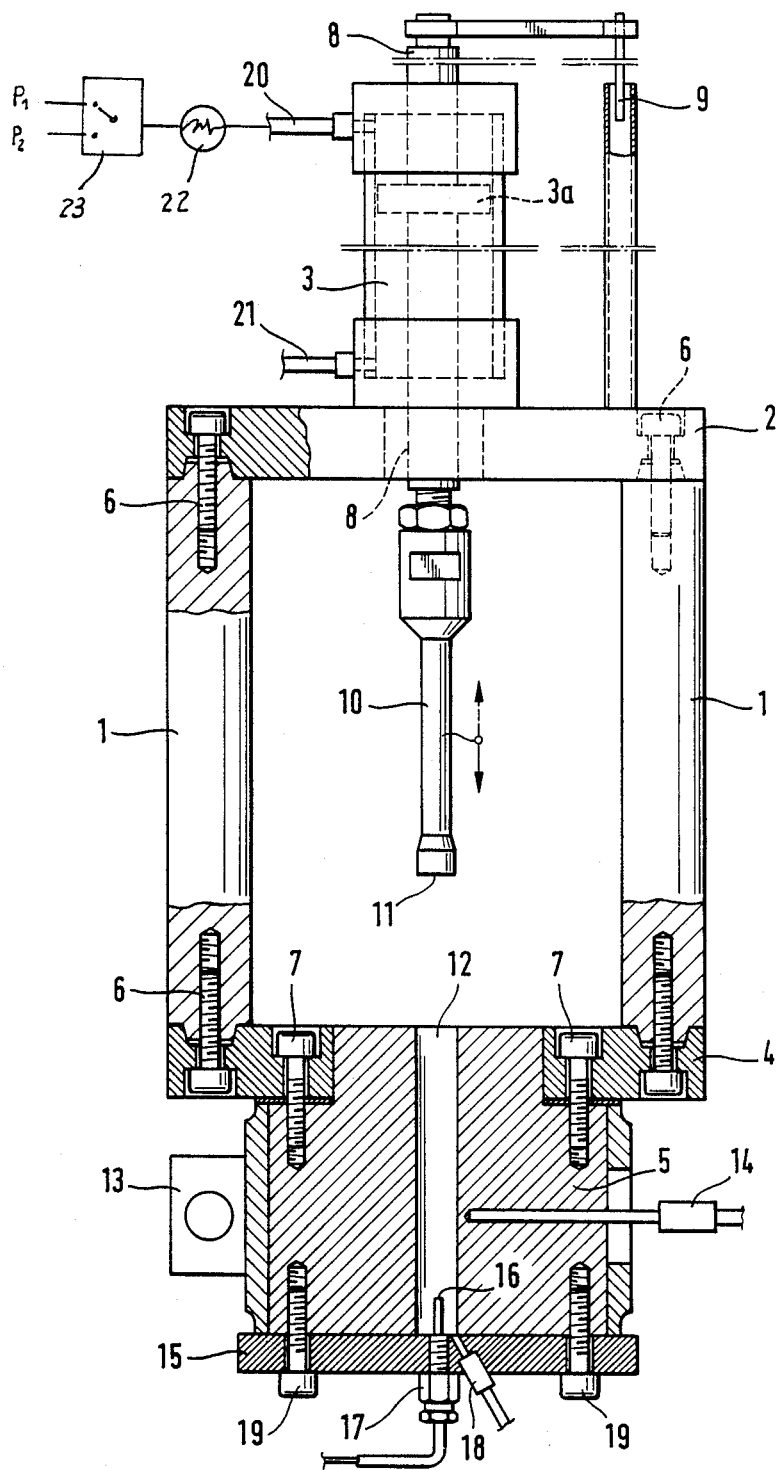

PROCESS FOR MEASURING THE VARIATIONS IN VOLUME OF FLUIDS, ESPECIALLY SHRINKAGE MEASUREMENTS IN SYNTHETIC RESINS DURING HARDENING AND A DEVICE FOR CARRYING OUT THE PROCESS

In the application of synthetic resins, a plurality of material properties and behaviour have to be measured and controlled during the differing phases of the treatment. The present invention relates in particular to the clarification of processes during the mould filling and hardening phases of duroplastic synthetic resins, and within this problem area, to the variation of density during a chemical reaction called shrinkage.

A number of shrinkage measuring processes are known, as are buoyancy methods, where the measuring of buoyancy is generally carried out in a heated oil bath. With known thermal expansion of oil and after measuring the tare and gross buoyancy, the density, i.e. the specific volume of the test piece can be calculated under isothermal conditions. However, no effective values can be obtained under non-isothermal conditions. Processes are also know where geometric variations to mould bodies are measured, for example variations in length or volume; however, here also the shrinkage can only be established in the solid phase under isothermal conditions, whilst the temperature curve cannot be measured at the same time. There are also various disadvantages attached to the remaining processes relating to measuring variations in length, such as the lack of temperature control and stability, the geometric influence of such moulded parts on the distribution of the shrinkage in three dimensions, the non-measurable shrinkage in the fluid phase, and the influence of the mould separating means. Furthermore, the shrinkage can be obtained in extremely specific applications by measuring a distortion of the substrate on to which the to be measured layer is applied; however, here also the shrinkage cannot be measured in the fluid phase with this process. In addition, there are also processes which even with the help of measuring the variation of electrical resistance, still cannot give full details about the shrinkage.

As opposed to this, it is the object of the present invention to provide a process for measuring volume variations in fluids, whereby in particular shrinkage measurements can be carried out where the reaction result takes place under non-isothermal conditions, incorporating the most important parameters. A further object is to provide a device for carrying out this process, whereby shrinkage measurements of a relatively simple kind can be carried out over the whole reaction period and given to a digital unit. A process and a device for carrying out this process which solve these objects are given in the claims.

The most extensively similar apparatus for relaxation testing of already finished premoulded thermoplastic test pieces in the form of tensile members or slabs are described in U.S. Pat. No. 4,069,703, GB.-A-No. 1,275,262 and FR.-A-No. 1,316,591. These test pieces are first fixed in the described apparatus after a separate manufacture has taken place, and are acted upon by means of tension i.e. force under the influence of temperature and their variation in length is measured. Differing from this, the device according to the invention can produce a test piece having extremely low viscose reactive fluids, and the process of the volume of which is followed during the moulding processes under the influence of pressure (tension) and temperature. From these observations one can determine the thermal expansion in the fluid and solid state and the shrinkage and relaxation times during the hardening process.

Furthermore, an apparatus is described in FR.-A-No. 2,377,042 for following the polymerization reaction of extremely high viscosity elastomer test pieces in tablet form. A tablet of rubber material is placed into a 3.5 mm tool which is open, and thereafter a closing pressure is exerted onto this tool. Conclusions about the degree of polymerization are drawn from the amount of overflowing material, and from the inner pressure of the mould. As opposed to this, the device according to the invention is a closed system whereby the overflowing material would have catastrophic results on the measuring results, as the relationship between the weighed amount of test piece and the volume would be disturbed.

The invention will now be described with reference to a drawing of an embodiment of a measuring device for measuring variations in volume, and where the single figure shows the device according to the invention.

On measuring variations in volume for synthetic resins, especially duroplastics, during the hardening phase, it is necessary to obtain homogeneous test pieces without blisters, fractured surfaces or shrinkage marks. Preliminary tests with a specific duroplastic resin system have shown that this is possible with a pressure of over 18 bar. It goes without saying that other values may be applicable for other synthetic resins. Therefore it is important in preliminary tests to impart the minimum pressure, above which perfect pouring is possible. Resulting from this knowledge, a device was constructed which satisfied the following requirements:

The measuring of pressure, temperature in the mould part and volume directly, simultaneously and independently from one another;
the smallest possible test piece volume;
a pressure range of 0–100 bar;
a temperature range of up to 250° C.;
simple to operate, above all for cleaning;
data should be able to be processed by means of a computer.

A device which satisfies the above requirements is shown in the FIG. The device has a framework with four uprights 1, to which an upper bearing plate 2 for the pressure cylinder 3 and a lower bearing plate 4 for the measuring cylinder 5 are secured by means of screws 6. The measuring cylinder 5 is secured to the lower bearing plate 4 by means of screws 7. The piston rod 8 of the pressure cylinder is connected to an inductive displacement detector 9, whereby the displacement of the measuring piston 10 can be measured very exactly. In the present invention the ratio of the piston surface 3a of the pressure cylinder to the measuring area 11 of the measuring cylinder 10 amounts to 9.33:1 and whereby a conversion ratio of the internal mould pressure of 1:9.33 results.

This internal mould pressure is produced by lowering the piston in the measuring bore 12. The measuring cylinder 5 can be brought to specific temperatures by means of a precisely controllable electrical heating means 13. These temperatures are determined by means of a measuring cylinder-temperature probe 14. A cover 15 is flange-mounted under the measuring cylinder 5, into which cover a thermo-element 16 in a pressure screw joint 17 is introduced exactly in the centre for determining the temperature inside the test piece. The thermo-element 16 must be introduced so far into the test piece that only that temperature will be detected, without any direct influence from the temperature of the measuring cylinder In the present example, with a bore diameter of 15 mm, the thermometer is introduced to a depth of 23 mm, measured from the end of the measuring cylinder. Calculations have shown that at this depth, the influence of parts not belonging to the test piece is small and can be disregarded. A piezoelectric pressure receiver 18, introduced through the cover, is located in the measuring bore 12, and flush with the surface of the measuring cylinder side of the cover. The cover is furthermore screwed to the measuring cylinder by means of screws 19.

The pressure cylinder 3 is acted upon by pressure via a pneumatic line, only the supply line 20 and the outlet 21 being shown. The pressure supplied is measured by means of a pressure gauge 22 in the pneumatic line, and from which the internal mould pressure can be calculated by means of the above given ratio. In addition, the pressure can be so selectively controlled by means of a pneumatic control 23, that two differing pressure levels can be alternately caused to act consecutively.

It is evident from the description of the apparatus having various probes and detectors, that the specific volume, temperature and pressure of the test piece as also the internal mould pressure and temperature of the measuring cylinder can be ascertained directly, simultaneously and independently from one another and under non-isothermal conditions. Preferably all the probes and detectors are connected with a digital unit—not shown here—so that the measuring data can be constantly received and processed.

Calculations show that with suitable probes and detectors, a maximum error in specific volume of 0.0002 cm$^3$/g is not exceeded. In a typical shrinkage measurement, the measuring bore is filled with a cold evacuated resin mixture after the tempering of the measuring cylinder, is immediately closed and is acted upon by pressure. Volume measurements can already supply valid data some 3s after filling. Immediately after that, by using a plurality of desired temperatures of from 60°–112° C. and internal mould pressures of 9.3 to 37.3 bar (corresponding to i.e. 4 bar atmospheric pressure), the variations in volume and test piece body temperature can be measured. From this a temperature profile can be attained and with the aid of same, the shrinkage can be calculated. So as to avoid the test piece body from losing contact with the cylinder wall after the gelling, either a specific internal mould pressure must prevail or the test piece must be coated with silicone oil. It has been found that 37.3 bar of internal mould pressure is sufficient to avoid an oil coating. Otherwise the test piece must be additionally coated with about 1 cm$^3$ of silicone oil, which necessitates a correction equalization of the oil on analysis, but which however can easily be ascertained with this device.

As already mentioned at the beginning, not only the shrinkage measurements are possible with this device but also other measurements relating to variations in volume. One can establish for example the variation of compression modulus and relaxation time with the aid of the pressure control, which allows two pressure levels., In addition, there is the possibility of ascertaining with the new device, the specific volume of fluid at various pressures up to 100 bar (compressibility) and temperatures to 250° C. (thermal expansion) in a single test piece, and of calculating simultaneously the gas content and compressibility of the ideal gas-free fluid from a series of measurements. Thus the fact that a gas allows itself to be more compressed than a fluid is exploited.

Ascertaining the gas content of fluids such as for example the air content in pouring or foam resins can be carried out with satisfactory exactitude with high portions, by comparing the density determinations of the gas-containing and evacuated resin in the pyknometer. However, if the gas content is <1% which leads with electro-casting resins to the influencing of the end properties, then more exact measuring procedures must be used. The device according to the invention enables a calculation of the gas content and compressibility of the ideal gas-free fluid to be made due to the simple operation and vary exact measuring of the specific volume with differing pressures (compressibility).

Proceeding from the equation of state of ideal gases: $p \cdot V = n \cdot R \cdot T =$ constant under isothermal conditions, one can obtain the following relationship between the specific volume of the ideal gas-free fluid $V_{sp,H}$, the compressibility of the ideal gas-free fluid $K$; and the volume portion of the gas at 1 bar normal pressure $V_G \left[ \dfrac{cm^3 \cdot 1\ bar}{g\ resin} \right]$ and the following equation is obtained:

$$K \cdot V_{sp,H} = \dfrac{V_{s1} - V_s}{p_2 - p_1} - \dfrac{V_G}{(p_1 + 1) \cdot (p_2 + 1)}$$

and where $V_{sl\ldots n}=$ the specific volume at pressure 1 ... n |bar|;
$p_1 \ldots n =$ internal mould pressure is 1 ... n |bar|.
The desired values, i.e. the volume portion of the gas at 1 bar normal pressure, as well as the compressibility of the ideal gas-free fluid can be calculated from this equation.

The described device is not tied to the given values so that both the dimensions of the measuring bore and the measuring piston which fits into same, and also the pressure relationship between the pressure piston surface and the surface of the measuring piston can have other values.

In addition, the measurement of the length of travel of the piston, i.e. of the piston rod 8 can be carried out in other ways than the inductive way for example in an optical way. In addition, the temperature of pressure cylinder 5 can be altered by means of a device other than an electrical heating means 13. That which is important is that the measuring of the travel of the measuring piston, the measuring of the pressure and of the temperatures take place directly and independently from one another, so that above all, nonisothermal conditions can be encompassed.

I claim:

1. A process for measuring variations in volume of a material comprising exerting a pressure upon the material to be measured such that a fully homogeneous test piece is obtained without any fractures or blisters and that simultaneously and independently from one another, the impinging pressure, the pressure exerted through the test piece, the temperature in the test piece and in its environs and the volume of the test piece are measured under non-isothermal conditions.

2. A process according to claim 1, wherein the measuring values are constantly detected and transmitted to a computing unit.

3. A process according to claim 1, wherein the specific volume of fluids is ascertained under varying pressures and temperatures, and from this the gas content and the compressibility of the ideal gas-free fluid are calculated.

4. The process of claim 1, wherein said material under test is a synthetic resin.

5. A process according to claim 4, wherein the pressure exerted on the test piece, should no oil coating be used, amounts to at least 18 bar for a duroplastic synthetic resin as the material under measurement.

6. A process according to claim 4, wherein the pressure impinges in an alternating manner on two differing levels so as to measure a variation of the compression module and the relaxation or retardation time during the hardening of the synthetic resin.

7. The process of claim 4, wherein said measuring is for measuring the shrinkage in said synthetic resin during the hardening thereof.

8. The process of claim 7, wherein the measuring values are detected before, during and after the hardening phase.

9. A device for measuring variations in volume of a material, comprising a measuring cylinder (5) comprising a measuring bore (12) and a measuring piston (10) which fits into this measuring bore and is acted upon by pressure, as well as a displacement detector (9) attached to the measuring piston, a first temperature probe (14) in the measuring cylinder, a second temperature probe (16) centrally positioned in the measuring bore for measuring the temperature in the test piece, a pressure gauge in the compressed air line, a pressure receiver (18) located at the end of the measuring bore opposite to the measuring piston and a heating means (13) for the measuring cylinder.

10. A device according to claim 9, wherein the pressure receiver is introduced into a removable cover (15) secured to the measuring cylinder.

11. A device according to claim 9, wherein the measuring piston (10) is acted upon by a pressure piston (3a), the effected surface of which amounts to a multiple of the effective surface (11) of the measuring piston.

12. A device according to claim 9 which also contains a framework comprising four uprights (1), with an upper plate (2) bearing the pressure cylinder (3) and a lower plater (4) bearing the measuring cylinder (5).

13. A device according to claim 9, wherein the compressed air line has a control, so that the compressed air can be caused to act in an alternative manner at two differing levels.

* * * * *